(12) United States Patent
Volker et al.

(10) Patent No.: US 8,583,407 B2
(45) Date of Patent: Nov. 12, 2013

(54) ULTRASONIC SURFACE MONITORING

(75) Inventors: Arno Willem Frederik Volker, Delft (NL); Thomas Geertruida Henricus Basten, Utrecht (NL)

(73) Assignee: Nederlandse Organisatie voor toegepast-natuurwetenschappelijk Onderzoek TNO, Delft (NL)

( * ) Notice: Subject to any disclaimer, the term of this patent is extended or adjusted under 35 U.S.C. 154(b) by 871 days.

(21) Appl. No.: 12/527,387

(22) PCT Filed: Feb. 19, 2008

(86) PCT No.: PCT/NL2008/050091
§ 371 (c)(1),
(2), (4) Date: Feb. 2, 2010

(87) PCT Pub. No.: WO2008/103036
PCT Pub. Date: Aug. 28, 2008

(65) Prior Publication Data
US 2010/0131246 A1    May 27, 2010

(30) Foreign Application Priority Data
Feb. 19, 2007    (EP) .................................. 07102653

(51) Int. Cl.
*G06G 7/48*    (2006.01)
(52) U.S. Cl.
USPC .................................................. 703/6; 703/1
(58) Field of Classification Search
USPC ............................................ 703/1, 6; 73/602
See application file for complete search history.

(56) References Cited

U.S. PATENT DOCUMENTS

| 5,767,408 A | 6/1998 | Lindgren et al. |
| 5,965,818 A | 10/1999 | Wang |
| 7,558,153 B2 * | 7/2009 | Zeroug et al. .................... 367/27 |
| 2005/0075846 A1 * | 4/2005 | Kim ................................. 703/1 |

FOREIGN PATENT DOCUMENTS

| GB | 2 383 413 A | 6/2003 |
| JP | 57 187609 A | 11/1982 |
| JP | 05-280953 A | 10/1993 |

(Continued)

OTHER PUBLICATIONS

Giurgiutiu, "Embedded Ultrasonics NDE with Piezoelectric Wafer Active Sensors", Jul. 7, 2009.*

(Continued)

*Primary Examiner* — Omar Fernandez Rivas
*Assistant Examiner* — Herng-Der Day
(74) *Attorney, Agent, or Firm* — Leydig, Voit & Mayer, Ltd.

(57) ABSTRACT

A method of modeling a surface of an object using ultrasonic transducers mounted on the surface by: providing a model of the surface comprising a primary set of surface points indicative of the height of the surface, transmitting pulsed waves from a first transducer to one or more second transducers along respective paths along the surface, measuring travel times of the pulsed waves along each path, calculating travel times based on the model of the surface, adjusting the model of the surface in response to any discrepancies between the measured travel times and the calculated travel times. The above steps are repeated until the discrepancies are smaller than a predetermined threshold. The step of calculating the travel times comprises interpolating the primary set of surface points in order to obtain an expanded secondary set of surface points, and the travel times are calculated using the expanded set.

12 Claims, 3 Drawing Sheets

(56) References Cited

FOREIGN PATENT DOCUMENTS

| JP | 2004-85515 A | 3/2004 |
|---|---|---|
| RU | 2138037 C1 | 9/1999 |
| SU | 461348 A1 | 2/1975 |
| SU | 1226301 A1 | 4/1986 |

OTHER PUBLICATIONS

Dobmann et al., "Nondestructive characterization of materials (ultrasonic and micromagnetic techniques) for strength and toughness prediction and the detection of early creep damage", Nuclear Engineering and Design, vol. 157, Issues 1-2, Jul. 1995, pp. 137-158.*

Lakestani et al., "Application of ultrasonic Rayleigh waves to thickness measurement of metallic coatings", NDT & E International, vol. 28, Issue 3, 1995, pp. 171-178.*

Leonard et al., *J Acoust Soc. Am.*, 114(2): 767-774(2003).

Leonard et al., iopscience.iop.org., http://iopscience.iop.org/0266-5611/18/6/322 1795-1808 (2002).

Berryman, *Mass. Inst. of Technology* (1990).

Kissling et al., *Physics of the Earth and Planetary Interiors*, 123; 89-101 (2001).

Blessing et al., "Ultrasonic Measurements of Surface Roughness" Applied Optics, OSA, Optical Society of America, vol. 32, No. 19, (Jul. 1, 1993), pp. 3433-3437.

International Search Report for PCT/NL2008/050091, dated Mar. 19, 2008.

* cited by examiner

ULTRASONIC SURFACE MONITORING

FIELD OF THE INVENTION

The present invention relates to ultrasonic surface monitoring. More in particular, the present invention relates to a method of and a device for modelling the surface of an object using ultrasonic transducers.

BACKGROUND

It is well known to use ultrasonic waves to obtain information on the surfaces of an object, for example a pole or pipe. Typically, ultrasonic pulses are transmitted towards the object, the reflected pulses are received and the travel times of the pulses are recorded. Any differences in travel times ("time of flight") of the pulses are indicative of differences in the relative height of the surface and hence of the wall thickness of the object. An example of this known technique is disclosed in U.S. Pat. No. 3,930,404. This type of method has the disadvantage that the measurements are extremely local: the surface is only probed at the points of impact (and reflection) of the ultrasonic waves. To obtain information on the remaining part of the surface, the ultrasonic transducers have to be moved relative to the object, and the travel times have to be measured in many other surface points.

International Patent Application WO 2006/000668 discloses a method for the dimensional characterisation of a cylindrical object. Probes facing measuring points on the surface of the object transmit pulsed ultrasonic waves to these measuring points and receive the reflected pulsed waves. To obtain dimensional information on the entire surface of the object without requiring an infinite number of measuring points, a characteristic curve of the surface is obtained by interpolation. Although information on other surface points can be obtained through interpolation, the level of detail of this information is limited by the number of measuring points. This known method therefore also has the fundamental disadvantage that surface information is obtained from only a small number of measuring points, and that a relative large number of probes and/or a movement of the probes relative to the object are necessary to obtain detailed dimensional information.

U.S. Pat. No. 5,965,818 discloses a method using ultrasonic Lamb waves to measure reduction of wall thickness due to localised corrosion at pipe supports. Two transducers are used to make a Lamb wave travel along the pipe wall in the circumferential direction. By comparing measured time-of-flight data the change in time-of-flight due to corrosion can be quantified. Corrosion is only detected in the circumferential direction of the pipe, not in the longitudinal direction.

U.S. Pat. No. 5,767,408 discloses a method of obtaining near-surface characteristics of a material by generating a broadband ultrasonic Rayleigh wave including a plurality of components. Velocities of selected components of the Rayleigh wave are determined at the selected frequencies. However, the wave trajectories are very limited and therefore the information concerning the surface tested is also limited.

British Patent Application GB 2 383 413 discloses a system for detecting defects in rails by using the velocity, attenuation, scattering, resonance and frequency absorbing properties of acoustic surface waves. This known system is quite specific to railway lines and uses electro-acoustic techniques to test rails in their longitudinal direction.

Japanese Patent Application JP 57 187609 discloses another conventional method of measuring wall thickness by using surface waves having an increasing frequency and detecting the travel times. The surface waves have limited trajectories in one direction only and therefore provide only limited information.

SUMMARY OF THE INVENTION

It is an object of the present invention to overcome these and other problems of the Prior Art and to provide a method of and a device for modelling the surface of an object by using ultrasonic transducers, which method and device provide more detail of the surface using a limited number of transducers.

It is a further object of the present invention to provide a method of and a device for modelling the surface of an object by using ultrasonic transducers, which method and device provide detailed information on the surface while requiring a limited computational effort.

Accordingly, the present invention provides a method of modelling a surface of an object using ultrasonic transducers mounted on the surface, the method comprising the steps of:
  providing a model of the surface, the model comprising a set of surface points indicative of the height of the surface,
  transmitting pulsed waves from a first transducer to one or more second transducers, the first transducer and each second transducer defining a respective path along the surface,
  measuring travel times of the pulsed waves along each path,
  calculating the travel times based on the model of the surface,
  adjusting the model of the surface in response to any discrepancies between the measured travel times and the calculated travel times, and
  repeating the steps of transmitting, measuring, calculating and adjusting until the discrepancies are smaller than a predetermined threshold,
wherein the step of calculating the travel times comprises the sub-step of interpolating the set of surface points in order to obtain an expanded set of surface points, the travel times being calculated using the expanded set.

By transmitting pulsed waves from a first transducer mounted on the surface to a second transducer mounted on the surface, the travel time of each pulsed wave depends on the path of the wave over and/or beneath the surface and therefore contains much more information than a single point measurement of the Prior Art discussed above which is based upon reflection instead of surface paths.

Repeatedly adjusting a surface model to better match the calculated and the measured travel times results in an optimal surface model which accurately predicts the travel times of the pulsed waves. Such techniques are known per se and are typically referred to as tomographic inversion or tomographic reconstruction. The resulting models may be displayed on a suitable display screen and/or analysed, for example to determine relatively thin parts of a pipe wall.

An important advantage of the present invention is the fact that only a limited number of surface points in used in the model, thus significantly reducing the number of calculations involved in the method. The accuracy of the model is not affected as the smaller number of surface points used in the model is compensated by interpolation. As a result, the expanded set of surface points used to adjust the model is much larger than the set of surface points of the actual model. In an advantageous embodiment, for example, the set of surface points is constituted by less than 100 points, preferably less than 50 points, while the expanded set of surface points is constituted by more than 200 points, preferably more than 500 points. Other numbers are also possible. For example, the model could use a set of only 20 surface points, while the expanded set has over 1000 surface points.

The height of the surface as modelled by the present invention is in most embodiments the height relative to the transducers. That is, the present invention models the relative height of the surface, taking the (absolute) height of the transducers as reference points. As the surface height of a wall of an object often is related to the thickness of the wall, the present invention also provides a model of the wall thickness of an object.

Several types of ultrasonic pulsed waves can be used in the present invention. In a first embodiment, the pulsed waves are Rayleigh waves. As Rayleigh waves propagate along the surface of the object, their travel time will be affected by variations in the (relative) height of the surface. Such variations may be caused by, for example, damage and/or corrosion. The variations in the measured travel times of these surface waves allow the model of the object to be adjusted accordingly.

In a second embodiment, the pulsed waves are guided waves. As the velocity of such waves depends on the wall thickness of the object, these waves are very suitable for modelling an object, in particular a hollow object. The wall thickness dependency of the pulsed waves is enhanced when dispersive pulsed waves are used.

Some types of waves, in particular dispersive waves, may become distorted while propagating along their paths. This distortion may result in an incorrect travel time measurement. Accordingly, a preferred embodiment of the present invention further comprises the step of applying a phase correction to the measured travel times of the pulsed waves.

The method of the present invention may be practised using only a single first transducer. However, it is preferred to use multiple first transducers. To allow an effective measurement of the respective travel times of the pulsed waves, it is preferred that the steps of transmitting pulsed waves and measuring travel times are carried out for at least two first transducers successively. By activating the first transducers successively, the waves they transmit can be detected separately. The time interval between successive transmissions of the first transducers will be related to the maximum possible deviation of the travel times.

Although any number of first transducers can be used, for example one, two, three, four or six, independent of the number of second transducers, it is preferred that the number of first transducers is equal to the number of second transducers.

In the modelling method defined above, guided waves and/or Rayleigh waves may be used. The inventors have realised that Rayleigh waves may also be used for surface scanning and/or detection in the absence of the modelling described above. Accordingly, the present invention provides as well a method of providing an evenness measure of a surface of an object using ultrasonic transducers mounted on the surface, the method comprising the steps of:
  transmitting pulsed waves from a first transducer to one or more second transducers, the first transducer and each second transducer defining a respective path along the surface,
  measuring travel times of the pulsed waves along each path, and
  calculating the evenness measure based on the measured travel times,
wherein the pulsed waves are Rayleigh waves.

The evenness measure may be expressed in a model of the surface, but this is not essential, and the evenness measure may be constituted by a single number indicative of the relative or absolute evenness of the surface.

The present invention further provides a method of monitoring a pipeline, the monitoring method comprising the modelling method according to any of the preceding claims. The monitoring method may further comprise the step of producing an alert when the height of the surface falls below a threshold value and/or when the model indicates that the pipeline has become weak.

The present invention also provides a computer program product for carrying out the method as defined above. A computer program product may comprise a set of computer executable instructions stored on a data carrier, such as a CD or a DVD. The set of computer executable instructions, which allow a programmable computer to carry out the method as defined above, may also be available for downloading from a remote server, for example via the Internet.

The present invention additionally provides a device for modelling a surface of an object using ultrasonic transducers mounted on the surface, the device comprising:
  a memory unit for storing a model of the surface, the model comprising a set of surface points indicative of the height of the surface,
  a first transducer and at least one second transducer, the first transducer and each second transducer defining a respective path along the surface,
  a transmission unit for transmitting pulsed waves along the respective paths from the first transducer to the one or more second transducers, and
  a processing unit arranged for:
    measuring travel times of the pulsed waves along each path,
    calculating the travel times based on the model of the surface,
    adjusting the stored model of the surface in response to any discrepancies between the measured travel times and the calculated travel times, and
    repeating the steps of transmitting, measuring, calculating and adjusting until the discrepancies are smaller than a predetermined threshold,
wherein the processing unit is further arranged for interpolating the set of surface points in order to obtain an expanded set of surface points, and for calculating the travel times using the expanded set.

The pulsed waves may be guided waves and/or Rayleigh waves. According to a further aspect of the present invention, Rayleigh waves may be used also in the absence of the modelling described above. The invention therefore also provides a device for providing an evenness measure of a surface of an object using ultrasonic transducers mounted on the surface, the device comprising:
  a first transducer and at least one second transducer, the first transducer and each second transducer defining a respective path along the surface,
  a transmission unit for transmitting pulsed waves along the respective paths from the first transducer to the one or more second transducers, and
  a processing unit arranged for:
    measuring travel times of the pulsed waves along each path, and
    a calculating the evenness measure based on the measured travel times,
wherein the pulsed waves are Rayleigh waves.

The present invention further provides a system for monitoring a pipeline, the system comprising a device as defined above, as well as at least one first transducer and at least one second transducer. Preferably, the device and the transducers are capable of communicating wirelessly.

BRIEF DESCRIPTION OF THE DRAWINGS

The present invention will further be explained below with reference to exemplary embodiments illustrated in the accompanying drawings, in which.

DETAILED DESCRIPTION OF THE DRAWINGS

Figure 1:
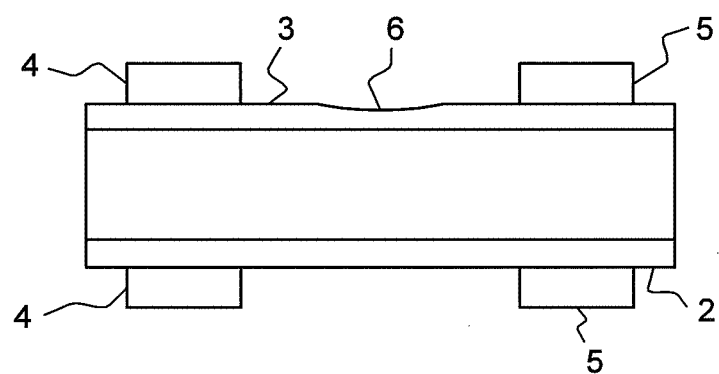
FIG. 1 schematically shows an object of which a surface is modelled in accordance with the present invention.

The pipe 2 shown merely by way of non-limiting example in FIG. 1 comprises a surface 3 which is to be modelled. In the example shown, the surface 3 has a recessed section 6 which may be caused by corrosion, for example. By suitably modelling the surface 3, the extent and (relative) height of the recessed section 6 may be determined.

First transducer units 4 and second transducer units 5 are mounted on the pipe 2, on either side of the surface 3. Although both the first and the second transducer units may be capable of transmitting and receiving ultrasonic waves, in the present invention the first transducer units 4 are used for transmitting ultrasonic pulsed waves while the second transducer units 5 are used for receiving these waves. The transducer units may be known per se and may be piezo-electric units.

Figure 2:
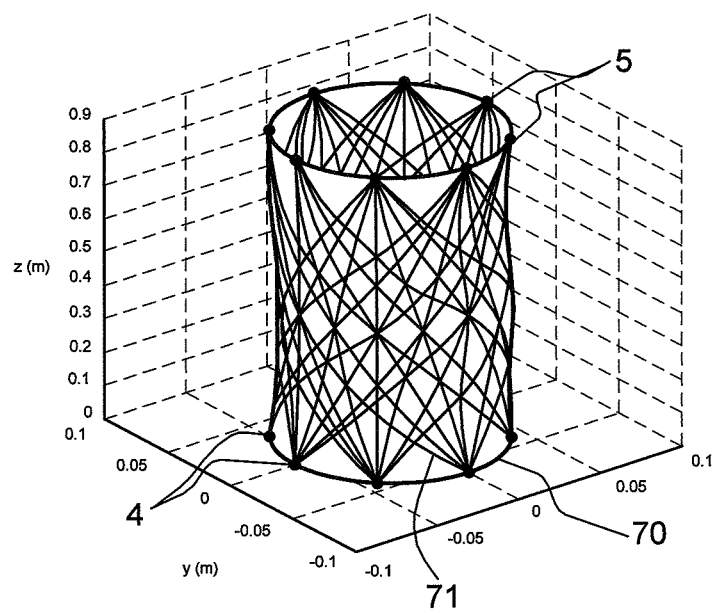
FIG. 2 schematically shows a 3-dimensional object model in accordance with the present invention.
Figure 3:
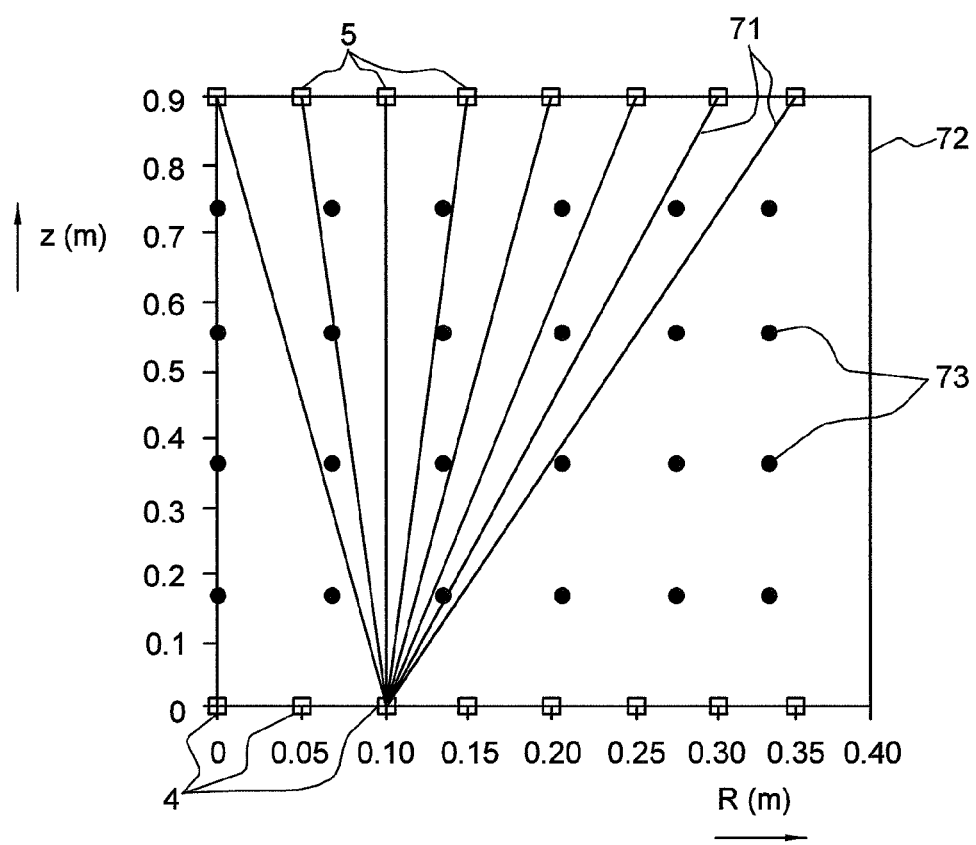
FIG. 3 schematically shows a 2-dimensional object model in accordance with the present invention.

The pulsed waves or pulses produced by the first transducers 4 have a defined duration of, for example, several µs (microseconds). The actual duration may depend on the particular application, for example the dimensions and mutual distances of the transducer units. The number of transducers may vary. At least one first transducer 4 and at least one second transducer 5 should be provided, although it is preferred to use multiple second transducers 5, for example two, three, four, eight of more second transducers 5. Using a plurality of second transducers 5 results in a plurality of paths traveled by the pulsed waves and hence an improved modelling of the surface. Similarly, it is preferred to use more than one first transducer 4. In the example of FIGS. 2 and 3, eight first transducers 4 and eight second transducers 5 are used, although the invention is not limited to these particular numbers. The transducers of a plurality of first and/or second transducers are preferably evenly spaced, although this is not essential.

An exemplary three-dimensional model is illustrated in FIG. 2, while the paths traveled by the pulsed waves and the reduction of surface points according to the present invention are illustrated by way of a two-dimensional model in FIG. 3. The three-dimensional model of FIG. 2 is based upon the two-dimensional model 72 of FIG. 3.

The model 70 of FIG. 2 represents the (outer) surface of a pipe, for example the pipe 2 of FIG. 1. The x-axis and y-axis extend in a cross-sectional plane of the tubular model, while the z-axis extends in its longitudinal direction. The dimensions of this example are provided in meters (m). The three-dimensional model of FIG. 2 is in fact a reconstruction of the object 2 of FIG. 1. Three-dimensional reconstructions are known per se in the field of tomography.

The surface modelled in FIG. 2 extends between a set of first transducers 4 and a set of second transducers 5. Paths 71 extend between each of the first transducer 4 and each of the second transducers 5. The travel times of the pulses along these paths are proportional to the lengths of the paths. A path which extends along a smooth, straight surface will be shorter than a path crossing the recess 6 of FIG. 1. Accordingly, the travel times along these paths will differ and the pulses will arrive at different times.

The model will calculate the arrival times of the pulses along the various paths. If the model initially assumes all paths to have equal lengths, a discrepancy between the measured travel times and the calculated travel times will occur for the paths crossing the recess 6. This discrepancy can be compensated by adjusting the model. Initial values of the model may be based upon measurements of the actual object (such as a pipe) and/or upon theoretical considerations.

In the two-dimensional example of FIG. 3, the horizontal axis extends along the circumference R of the tubular model, while the z-axis extends in its longitudinal direction. The dimensions are provided in meters (m).

As can be seen in FIG. 3, first transducers 4 and second transducers 5 are evenly spaced along the circumference of the model. Pulses produced by the first transducers will be detected by the second transducers. The arrival times, and hence the travel times, will correspond at least approximately to the set of paths 71 extending between each first transducer 4 and the second transducers 5. For the sake of clarity of the drawing, only one such set of paths 71 is shown in FIG. 3.

As explained above, the model contains information about the surface (3 in FIG. 1) of the object. This information may comprise a set of values representing the (relative or absolute) height of the surface in a number of points. As illustrated in FIG. 1, the surface height at the recess 6 is smaller than at the first transducer 4. In order to accurately model the surface, a large number of surface points are required, for example hundreds or even thousands of surface points. However, determining the surface points directly from the measured travel times would require a very large number of computations. For this reason, the invention provides a more efficient model which contains only a limited number of surface points, thus significantly reducing the number of computations.

In accordance with the present invention, the model contains only a limited set of surface points 73. These "core" surface points are stored in the model and are adjusted if necessary to match the observed travel times. In the example shown, only 24 surface points are used in the model, thus providing a significant saving compared with the hundreds or thousands of points mentioned above. It will be understood that the number of "core" surface points may vary depending on the dimensions of the surface modelled and the accuracy required, and that this number may equally well be greater or smaller than 24, for example 16, 30 or 50.

In order to accurately model the surface and calculate the travel times, a larger number of surface points are typically required. According to a further aspect of the present invention, an expanded set of surface points is obtained through interpolation. That is, the set of surface points of the model ("core" surface points) is interpolated to provide an expanded set of surface points used for calculating travel times and providing more detailed surface information, if required. In this way, the exemplary number of 24 surface points may be expanded to, for example, 1024 surface points.

The model used in the present invention can therefore be considered a two-level model. On a basic level, a limited set of (for example 24) surface points is determined and stored. These "core" surface points are adjusted in accordance with the measured travel times. On a higher level, an expanded set of (for example 1024) surface points is determined by interpolation and (temporarily or permanently) stored. These "expansion" surface points are therefore derived indirectly from the measured travel times, unlike the "core" surface points which are derived directly.

Using the expanded set, the travel times according to the model can be accurately determined using numerical techniques which may be known per se. Typically, each path 71 is divided into a large number of sections. For each path, the travel times of all path sections is calculated, using the height information contained in the set of expanded surface points derived from the model. Then the travel time of each path is determined by adding the travel times of the sections of the particular path, resulting in the calculated travel times.

The measured travel times are determined by subtracting transmission times of pulses from their arrival times. The transmission times are typically determined by recording the points in time at which an activation signal is sent to a first transducer unit, while the arrival times are typically determined by recording the points in time at which detection signals are received from the second transducer units.

Then the calculated travel times are compared with the measured travel times and any discrepancies are recorded. An optimisation procedure, which may be known per se, is then used to optimise the model such that the discrepancies are removed. Suitable known optimisation procedures are the Levenberg-Marquardt and the Gauss-Newton procedures.

In the method of the present invention, surface waves are used. Surface waves have the advantage that each pulse obtains information of a path, not just a point. It has been found that Rayleigh waves are very suitable surface waves as they follow the surface. As a result, their travel times provide very accurate information on the surface structure.

However, guided waves are also very suitable, in particular when not only information concerning the surface but also concerning the wall thickness of the object is required. In particular, the advantageous dispersive behaviour of guided waves is utilized: given the frequency, the propagation velocity of the waves depends on the wall thickness. Accordingly, any measured velocity changes are indicative of wall thickness variations.

A combination of Rayleigh (pulsed) waves and surface (pulsed) waves may also be used.

According to a further aspect of the present invention, Rayleigh waves may be used for providing an evenness measure of a surface, also in the absence of a reconstruction model as shown in FIG. 2. That is, a method of providing an evenness measure of a surface of an object by using ultrasonic transducers mounted on the surface may comprise the steps of transmitting pulsed waves from a first transducer to one or more second transducers, the first transducer and each second transducer defining a respective path along the surface, measuring travel times of the pulsed waves along each path, and calculating the evenness measure based on the measured travel times, the pulsed waves being Rayleigh waves. Accordingly, Rayleigh waves may be used with or without a model of the surface. The (un)evenness measure may be a suitable number (for example in a range from 1 to 10) or any other suitable measure.

The evenness measure may be, for example, inversely proportional to the (relative) travel times, that is, to the delay caused by the unevenness. A short delay will indicate a high degree of evenness (and hence a relatively high value of the evenness measure), while a longer delay will be indicative of a lower evenness. Hence, the relative time delays of the Rayleigh waves can be used to determine an evenness measure. A reference time delay representing a "perfect" evenness may be determined on the basis of theoretical considerations or an actual measurement using a very even surface.

According to a further aspect of the present invention, a phase correction may be used to correct dispersive waves. This is schematically illustrated in FIGS. 4A and 4B, where FIG. 4A shows an original pulse 81 (thick line) and its distorted counterpart 82 (thin line), while FIG. 4B shows a reconstructed pulse 83.

Figure 4A:
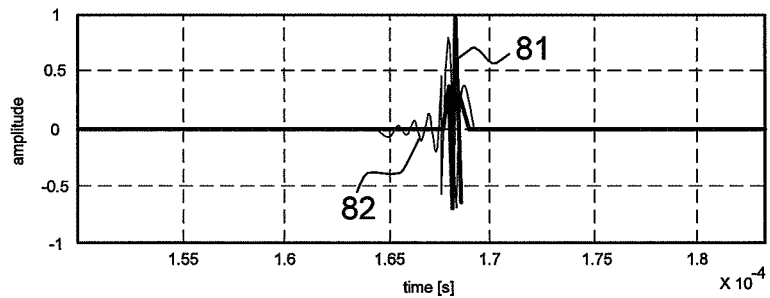
FIGS. 4A & 4B schematically show ultrasonic pulses used in the present invention.
Figure 4B:
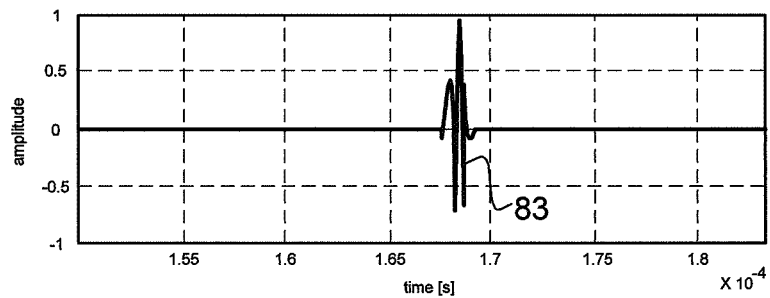

In FIG. 4A, a pulse 82 is shown to be distorted due to dispersion: the original phase relationship of the pulse is lost and the pulse is spread out in time, as compared to the original pulse 81. This makes the determination of the arrival time of the pulse, and hence its travel time, less accurate.

This loss of accuracy may be avoided by applying an (optional) phase correction X. In an exemplary embodiment, the phase correction X may be expressed as:

$$X = \exp^{-i\omega\left(\frac{x}{v(\omega_c)} - \frac{x}{v(\omega)}\right)}$$

where ω is the (angular) frequency, v(ω) is the frequency-dependent propagation velocity of the pulses, and x is the path length in the absence of any recesses or protrusions on the surface.

This correction may be applied by subjecting the distorted pulse 82 to a fast Fourier transform (FFT), multiplying the resulting spectrum by the phase correction X, and then applying an inverse fast Fourier transform (IFFT) to obtain the corrected pulse 83. After correction, the phase and hence shape of the pulse is restored, as illustrated in FIG. 4B. This restored pulsed wave 83 allows an accurate detection of its travel time. Those skilled in the art will realise that other phase correction techniques may be applied, for example using a predictive error filter.

Figure 5:
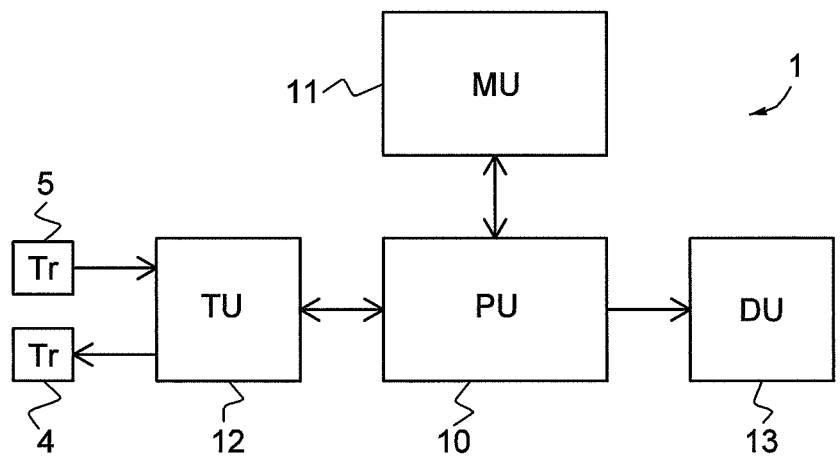
FIG. 5 schematically shows a surface modelling device according to the present invention.

A device for modelling a surface of an object is illustrated in FIG. 5. The device 1 comprises a processing unit (PU) 10, a memory unit (11), a transmission unit (TU) 12 and a display unit (DU) 13. The processing unit 10 preferably comprises a microprocessor capable of executing instructions of a software programme embodying the method of the present invention. The memory unit 11 may store this software programme, as well as parameters of the model, including the set of surface point values. The display unit 13 preferably comprises a display screen capable of displaying the model, in particular a reconstruction of the type illustrated in FIG. 2. The transmission unit 12 is capable of producing, under control of the processing unit 10, pulse transmission signals which are fed to the first transducer(s) 4. In addition, the transmission unit 12 is capable of receiving pulse detection signals produced by the second transducer(s) 5 and feeding suitable pulse detection information to the processing unit 10.

The transmission unit 12 may be arranged for wireless communication with the transducers 4 and 5, for example using radio frequency (RF) communication or infrared communication. The processing unit 10 may additionally be arranged for applying a phase correction as discussed above. Suitable programme steps for phase correction may be stored in the memory unit 11.

A device for providing an evenness measure of a surface may also have a structure as illustrated in FIG. 5.

It will be understood that the invention is not limited to pipes or tubes but may also be applied on the surfaces or walls of other objects, for example (parts of) ship hulls, airplane fuselages, car bodies, tank armour, or other surfaces or wall structures, for example storage tanks, rods, steel bridges, and metal structures in buildings.

The present invention is based upon the insight that the computational load of modelling a surface may be significantly reduced by using a model having a limited number of surface points, and that the accuracy of the model may be maintained by interpolating the surface points used in the model. The present invention benefits from the further insight that Rayleigh waves are very suitable for gathering surface information.

It is noted that any terms used in this document should not be construed so as to limit the scope of the present invention. In particular, the words "comprise(s)" and "comprising" are not meant to exclude any elements not specifically stated. Single elements may be substituted with multiple elements or with their equivalents.

It will be understood by those skilled in the art that the present invention is not limited to the embodiments illustrated above and that many modifications and additions may be made without departing from the scope of the invention as defined in the appending claims.

The invention claimed is:

1. A method of modeling a surface of an object using ultrasonic transducers mounted on the surface, the method comprising the steps of:
   providing a model of the surface, the model comprising a set of surface points indicative of a height of the surface,
   transmitting pulsed waves from a first transducer to one or more second transducers, the first transducer and each one of the one or more second transducers defining a respective path along the surface,
   measuring travel times of the pulsed waves along each path,
   calculating travel times based on the model of the surface,
   adjusting the model of the surface in response to a discrepancy between a measured travel time and a calculated travel time for a path along the surface, and
   repeating the steps of transmitting, measuring, calculating and adjusting until any discrepancies between the measured travel time and the calculated travel time for paths along the surface are smaller than a predetermined threshold,
   wherein the step of calculating travel times comprises a sub-step of interpolating between points of the set of surface points to obtain an expanded set of surface points, the travel times being calculated using the expanded set.

2. The method according to claim 1, wherein the set of surface points contains less than 100 points, and the expanded set of surface points contains more than 200 points.

3. The method according to claim 1, wherein the pulsed waves are guided waves.

4. The method according to claim 1, wherein the pulsed waves are Rayleigh waves.

5. The method according to claim 1, further comprising the step of applying a phase correction to the measured travel times of the pulsed waves.

6. The method according to claim 1, wherein the steps of transmitting pulsed waves and measuring travel times are carried out for at least two first transducers successively.

7. The method according to claim 6, wherein the number of first transducers is equal to the number of second transducers.

8. The method according to claim 1, wherein the object is a pipeline.

9. A non-transitory computer-readable medium including computer-executable instructions for carrying out a method comprising the steps of:
   providing a model of a surface, the model comprising a set of surface points indicative of a height of the surface,
   transmitting pulsed waves from a first transducer to one or more second transducers, the first transducer and each one of the one or more second transducers defining a respective path along the surface,
   measuring travel times of the pulsed waves along each path,
   calculating travel times based on the model of the surface,
   adjusting the model of the surface in response to discrepancy between a measured travel time and a calculated travel time for a path along the surface, and
   repeating the steps of transmitting, measuring, calculating and adjusting until any discrepancies between the measured travel time and the calculated travel time for paths along the surface are smaller than a predetermined threshold,
   wherein the step of calculating travel times comprises a sub-step of interpolating between points of the set of surface points obtain an expanded set of surface points, the travel times being calculated using the expanded set.

10. A device for modeling a surface of an object using ultrasonic transducers mounted on the surface, the device comprising:
    a memory unit for storing a model of the surface, the model comprising a set of surface points indicative of a height of the surface,
    a first transducer and at least one second transducer, the first transducer and each one of the at least one second transducer defining a respective path along the surface,
    a transmission unit for transmitting pulsed waves along the respective paths from the first transducer to the at least one second transducers, and
    a processing unit arranged for:
       measuring travel times of the pulsed waves along each path,
       calculating the travel times based on the model of the surface,
       adjusting the model of the surface in response to a discrepancy between a measured travel time and a calculated travel time for a path along the surface, and
       repeating the steps of transmitting, measuring, calculating and adjusting until any discrepancies between the measured travel time and the calculated travel time for paths along the surface are smaller than a predetermined threshold,
       wherein the processing unit is further arranged for interpolating between points of the set of surface points to obtain an expanded set of surface points, and for calculating the travel times using the expanded set.

11. The device according to claim 10, wherein the object is a pipeline.

12. The device according to claim 10, wherein the processing unit and the transducers communicate wirelessly.

* * * * *

UNITED STATES PATENT AND TRADEMARK OFFICE
CERTIFICATE OF CORRECTION

PATENT NO. : 8,583,407 B2  
APPLICATION NO. : 12/527387  
DATED : November 12, 2013  
INVENTOR(S) : Volker et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1059 days.

Signed and Sealed this
Twenty-second Day of September, 2015

Michelle K. Lee
*Director of the United States Patent and Trademark Office*